United States Patent
Puder

(10) Patent No.: US 7,527,123 B2
(45) Date of Patent: May 5, 2009

(54) PATIENT-FRIENDLY STETHOSCOPE

(75) Inventor: Mark Puder, Medfield, MA (US)

(73) Assignee: Children's Medical Center Corporation, Boston, MA (US)

( * ) Notice: Subject to any disclaimer, the term of this patent is extended or adjusted under 35 U.S.C. 154(b) by 310 days.

(21) Appl. No.: 11/438,599

(22) Filed: May 22, 2006

(65) Prior Publication Data

US 2006/0260865 A1 Nov. 23, 2006

Related U.S. Application Data

(60) Provisional application No. 60/683,832, filed on May 23, 2005.

(51) Int. Cl.
*A61B 7/02* (2006.01)
*A61B 7/04* (2006.01)
*A61B 5/02* (2006.01)
*H04M 1/22* (2006.01)

(52) U.S. Cl. .................. 181/131; 362/86; 381/67; 600/528

(58) Field of Classification Search ................ 181/131; 600/528; 362/86; 381/67
See application file for complete search history.

(56) References Cited

U.S. PATENT DOCUMENTS

| 4,577,638 | A | * | 3/1986 | Graham | 600/484 |
|---|---|---|---|---|---|
| 4,672,975 | A | * | 6/1987 | Sirota | 600/528 |
| 4,783,813 | A | * | 11/1988 | Kempka | 381/67 |
| 5,813,992 | A | * | 9/1998 | Henwood | 600/528 |
| 5,920,038 | A | * | 7/1999 | Foster | 181/131 |
| 5,989,186 | A | | 11/1999 | Alatriste | |
| 6,005,951 | A | * | 12/1999 | Grasfield et al. | 381/67 |
| 6,165,035 | A | * | 12/2000 | Avner | 446/72 |
| 6,202,784 | B1 | | 3/2001 | Alatriste | |
| 6,454,045 | B1 | * | 9/2002 | Ryan | 181/131 |
| D485,357 | S | * | 1/2004 | Kapinos, Sr. | D24/134 |
| D490,923 | S | | 6/2004 | Costa et al. | |
| 2002/0107579 | A1 | | 8/2002 | Makino | |
| 2003/0072457 | A1 | * | 4/2003 | Grasfield et al. | 381/67 |
| 2003/0208130 | A1 | * | 11/2003 | Yotam et al. | 600/528 |
| 2004/0102804 | A1 | | 5/2004 | Chin | |
| 2004/0107610 | A1 | * | 6/2004 | Gulati | 40/316 |
| 2004/0111101 | A1 | | 6/2004 | Chin | |
| 2004/0225191 | A1 | | 11/2004 | Sekine et al. | |
| 2004/0249298 | A1 | * | 12/2004 | Selevan | 600/528 |
| 2007/0103926 | A1 | * | 5/2007 | Brooks et al. | 362/555 |

* cited by examiner

*Primary Examiner*—Jeffrey Donels
*Assistant Examiner*—Christina Russell
(74) *Attorney, Agent, or Firm*—Altera Law Group, LLC

(57) ABSTRACT

Generally, the present invention is directed to medical devices and more particularly to a patient-friendly stethoscope with interactive light emissions. An embodiment of the invention includes a stethoscope which has a pair of binaurals and a transparent acoustical tubing connecting the binaurals to the chestpiece. An optical fiber is located within the transparent acoustical tubing extending from the junction region of the tubing to and within the chestpiece, thereby illuminating the chestpiece, the rim of the diaphragm and bell, and attachments to the chestpiece. The optical fiber has a light source coupled at its proximal end thereby illuminating the transparent acoustical tubing, the chestpiece, and attachments thereto from within.

11 Claims, 6 Drawing Sheets

PATIENT-FRIENDLY STETHOSCOPE

CROSS REFERENCE TO RELATED APPLICATIONS

This application claims the benefit of U.S. Provisional Application No. 60/683,832 filed 23 May 2005, which hereby is incorporated herein by reference in its entirety.

FIELD OF THE INVENTION

The present invention is directed generally to medical devices and more particularly to a patient-friendly stethoscope with interactive light emissions.

BACKGROUND

Stethoscopes are a tried and true medical device used in hospitals and medical facilities throughout the modern world for many decades. In many instances, the stethoscope is the first tool a physician or nurse uses to evaluate the general condition of a new patient. To an adult, the stethoscope is normally a non-threatening device and no detailed explanation is generally needed to coerce the patient to remove their shirt or blouse for an initial examination. Children, especially small children, may view the stethoscope in an entirely different mind set. For example, a small child just awakening from surgery in the recovery room, disoriented and already sensitive to the pre-surgery work up of blood draws and physicians poking and prodding them, may be initially and unnecessarily alarmed by the image of yet another health care professional coming at them with something to probe their body.

In a less extreme, but none the less possibly unnerving experience for a small child, the experience of being awoken in the middle of the night during normal hospital rounds, again somewhat disoriented in unfamiliar surroundings only to find a health care professional ready to probe them once again with a shiny metal object, should be undertaken with care and understanding.

Given the above, it would be desirable to have a stethoscope device whose physical appearance is engaging to a small child, almost to the point where it could be mistaken for a toy wherein the child reaches out for it instead of recoiling from it.

SUMMARY OF THE INVENTION

Generally, the present invention relates to medical devices and more particularly to a patient-friendly stethoscope with interactive light emissions.

One particular embodiment of the invention is directed to a stethoscope having an optically illuminated transparent acoustical tubing. The stethoscope has a pair of binaurals and a transparent acoustical tubing connecting the binaurals to the chestpiece. An optical fiber is located within the transparent acoustical tubing extending from the junction region of the tubing to the chestpiece. The optical fiber has a light source coupled at its proximal end thereby illuminating the transparent acoustical tubing from within.

Another embodiment of the invention is directed to a stethoscope having an optically illuminated transparent acoustical tubing. The stethoscope has a pair of binaurals and a transparent acoustical tubing connecting the binaurals to the chestpiece. An optical fiber is located within the transparent acoustical tubing extending from the junction region of the tubing to the chestpiece. The optical fiber is impregnated with a fluorescent dye and a light source is coupled at its proximal end for exciting the fluorescent dye thereby illuminating the transparent acoustical tubing from within.

Another embodiment of the invention is directed to a stethoscope having an optically illuminated transparent acoustical tubing. The stethoscope has a pair of binaurals and a transparent acoustical tubing connecting the binaurals to the chestpiece. The transparent acoustical tubing is impregnated with a phosphor material thereby illuminating the transparent acoustical tubing from within.

Another embodiment of the invention is directed to a stethoscope having an optically illuminated chestpiece (via optical fibers, luminescent materials, direct illumination, such as LEDs or other means known to a person skilled in the art). The stethoscope has a pair of binaurals and an acoustical tubing connecting the binaurals to the chestpiece. The chestpiece is impregnated with a phosphor material thereby illuminating the chestpiece from within.

Another embodiment of the invention is directed to a method of making a stethoscope attractive and non-threatening to a child by providing the acoustic tubing of the stethoscope with a source of illumination and activating the illumination when the child is being examined and thereby distracted.

Another embodiment of the invention is directed to a stethoscope having a heat responsive coating on part of the stethoscope, wherein the heat responsive coating produces different colors in response to different temperatures.

Another embodiment of the invention is directed to a patient-friendly medical instrument for measuring a metabolic parameter of a patient, wherein an illumination source covering a portion of the instrument responds to the metabolic stimulation applied to the instrument.

Another embodiment of the invention is directed to an ultrasound device having an optically illuminated transparent outer tubing. An optical fiber is located within the transparent outer tubing for internally illuminating the outer transparent tubing from within. The optical fiber has a light source coupled at its proximal end thereby illuminating the transparent acoustical tubing from within.

Another embodiment of the invention is directed to an ultrasound device having an optically illuminated transparent outer tubing. An optical fiber is located within the transparent outer tubing for internally illuminating the outer transparent tubing from within. The optical fiber is impregnated with a fluorescent dye and a light source is coupled at its proximal end for exciting the fluorescent dye thereby illuminating the transparent outer tubing from within.

Another embodiment of the invention is directed to an ultrasound device having an optically illuminated transparent outer tubing. The transparent outer tubing is impregnated with a phosphor material for internally illuminating the outer transparent tubing from within. The impregnated phosphor material may extend from the proximal end of the ultrasound probe to the distal end of the ultrasonic probe.

Another embodiment of the invention is directed to an endoscope device having an optically illuminated transparent outer tubing. An optical fiber is located within the transparent outer tubing extending from the proximal end of the endoscope to the distal end of the endoscope. The optical fiber has a light source at its proximal end thereby illuminating the transparent outer tubing from within.

Another embodiment of the invention is directed to an endoscope device having an optically illuminated transparent outer tubing. An optical fiber is located within the transparent outer tubing for internally illuminating the outer transparent tubing from within. The optical fiber is impregnated with a fluorescent dye and a light source is coupled at its proximal end for exciting the fluorescent dye thereby illuminating the transparent outer tubing from within.

Another embodiment of the invention is directed to an endoscope device having an optically illuminated transparent outer tubing. The transparent outer tubing is impregnated with a phosphor material for internally illuminating the outer transparent tubing from within. The impregnated phosphor material may extend from the proximal end of the endoscope to the distal end of the endoscope.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 8 shows the chestpiece of the patient-friendly stethoscope wherein the outer rim of the diaphragm and bell areas have been impregnated with phosphor material or is illuminated by fiber optics, direct illumination sources or similar.

Figure 1:
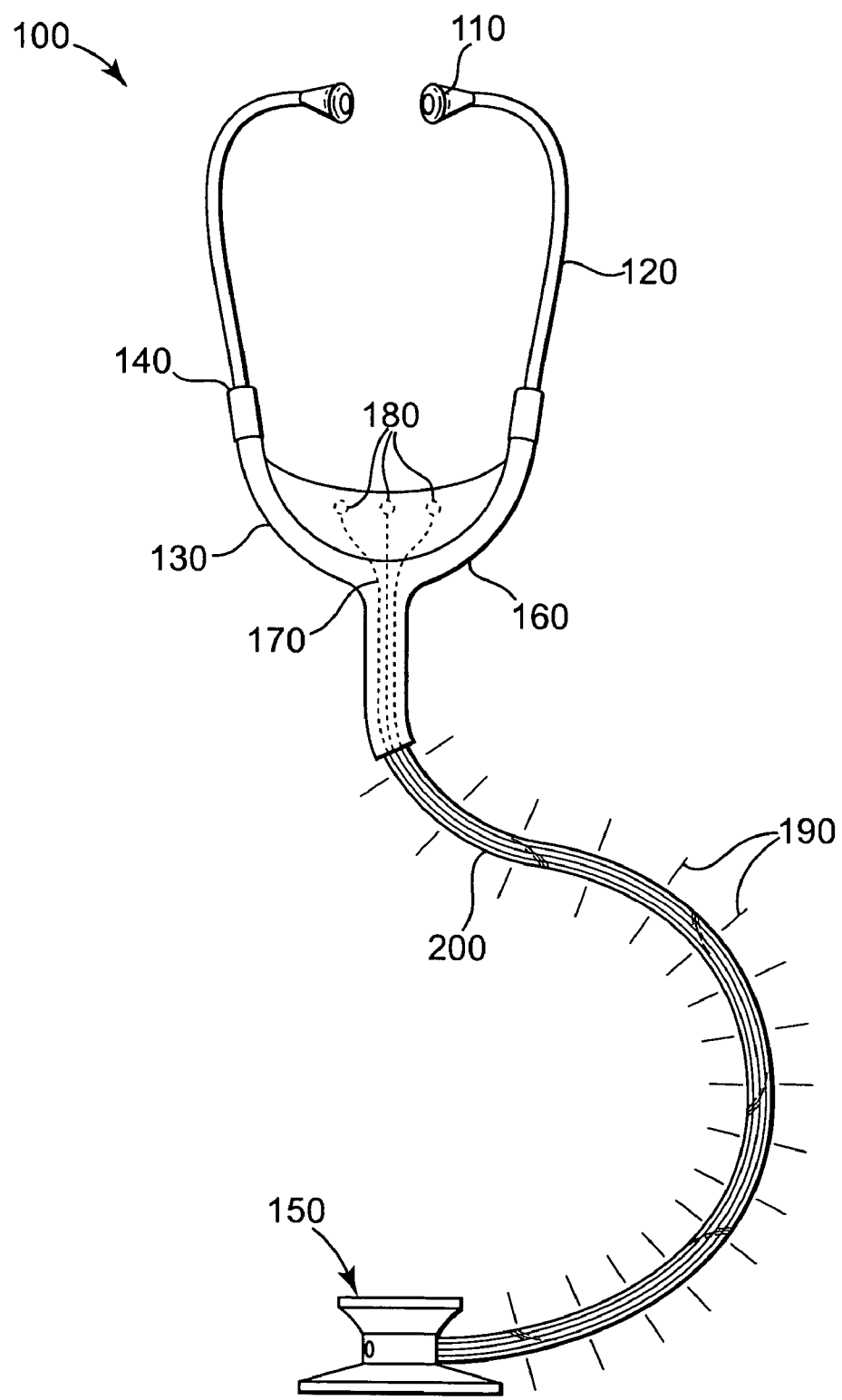
FIG. 1 shows a patient-friendly stethoscope with light emanating from the flexible region of the device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Medical treatment of children is more than pure medical science. It involves providing a friendly and welcoming environment to be able to effectively gain the patient's cooperation and trust. A nervous patient may not only be uncooperative, but may be so nervous that performing the exam, test, or diagnostic may either be impossible, or the results so skewed by an upset patient, that a misdiagnosis may occur. Consequently, a medical practitioner would be well served by instruments and tools which are attractive rather than frightening.

A stethoscope is one of the first instruments which a patient may encounter, so we focus on this tool as an example of how such devices may be modified to make them attractive and fun to the young patient. To avoid an overly long patent application, we do not detail the application of these concepts to the thousands of medical instruments to which they can be applied (e.g., ultrasound probes, endoscopes, etc.), but this is implicit in our disclosure.

In general, the present invention is directed to medical devices and more particularly to a patient-friendly stethoscope with features which make is attractive, interesting or non-threatening to adolescent-patients. While this disclosure is written around the use of such features such as interactive light emissions, from a stethoscope, the principles are fully applicable to other medical devices which a patient may encounter during examination and treatment. FIG. 1 shows a patient friendly stethoscope 100 with added features to make the device engaging to a small child. The stethoscope 100 has a pair of plastic earpieces 110 attached to a set of metal binaurals 120. In the traditional stethoscope, the metal binaurals 120 typically have a flexible opaque acoustic tubing 130 over its bottom shaft which may extend from the end 140 of the metal binaurals 120 for approximately 18 inches to the chestpiece 150. In the patient friendly stethoscope 100 the opaque acoustic tubing 130 may only extend from the end of the metal binaurals 120 to approximately 2 to 3 inches beyond the junction region 160 of the "Y" shaped opaque acoustic tubing 130, then on to a further acoustical tube 200 and to the chest piece 150.

Note that there are electronic versions of the above which are also applicable to this invention. The acoustical tube or conduit 200 need not be a tube at all, but merely a conduit for sound signals, whether, acoustical, analog or digital electrical or optical, or other means presently available.

In the patient friendly stethoscope 100, a plurality of "leaky" optical fibers 170 or other light radiating structures may extend from just above the Y junction region 160 down to the chest piece 150. By leaky, we refer to those optical fibers which radiate or scatter light energy outward continuously along the length of the fiber. Light emitting devices 180 may be optically coupled to the optical fibers 170 by means well known in the art of optical communications. The optical fibers 170 may be protected from direct physical damage by a transparent acoustic tubing or conduit 200 or other suitable material. FIG. 1 depicts one particular embodiment of the present invention wherein three light emitting devices 180 are each individually coupled to a specific optical fiber 170. In this embodiment, the three light emitting devices 180 may be a red, green, and blue light source each with their own on/off button or equivalent mechanism. In this configuration, when the physician or nurse activates one of the light emitting devices 180, the corresponding optical fiber 170 may outwardly radiate light 190 over the entire length of the fiber to the chest piece 150. Given the above, the physician or nurse may manually change the color of the stethoscope 100 at will to make the stethoscope more enticing to a child patient.

Figure 2:
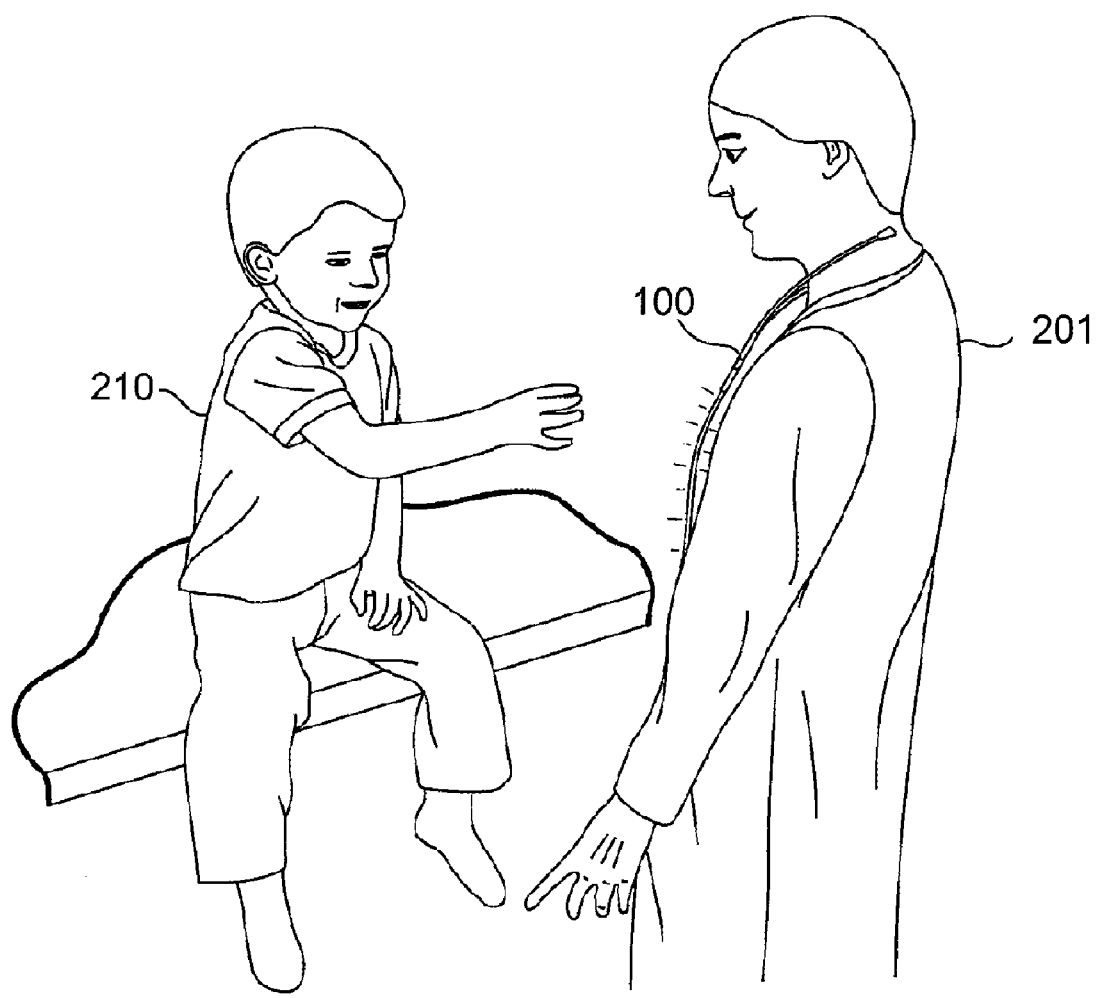
FIG. 2 shows a small child on the exam table reaching for the physician's lighted stethoscope.

In an alternative embodiment, the patient-friendly stethoscope 100 may have on-board electronics which may repetitively flash or switch from one light emitting device 180 to another (i.e., switching colors) in a pre-determined or random fashion, all with the goal of making the stethoscope 100 enticing to the child patient. FIG. 2 shows one possible desired result of the patient-friendly stethoscope 100, wherein the physician 201 has just entered the exam room and the child patient 210 is sufficiently enamored with the "lighted" stethoscope 100 that they reach for it and hopefully make the physician's job easier when ultimately using the stethoscope 100 for its designed medical function.

Figure 3:
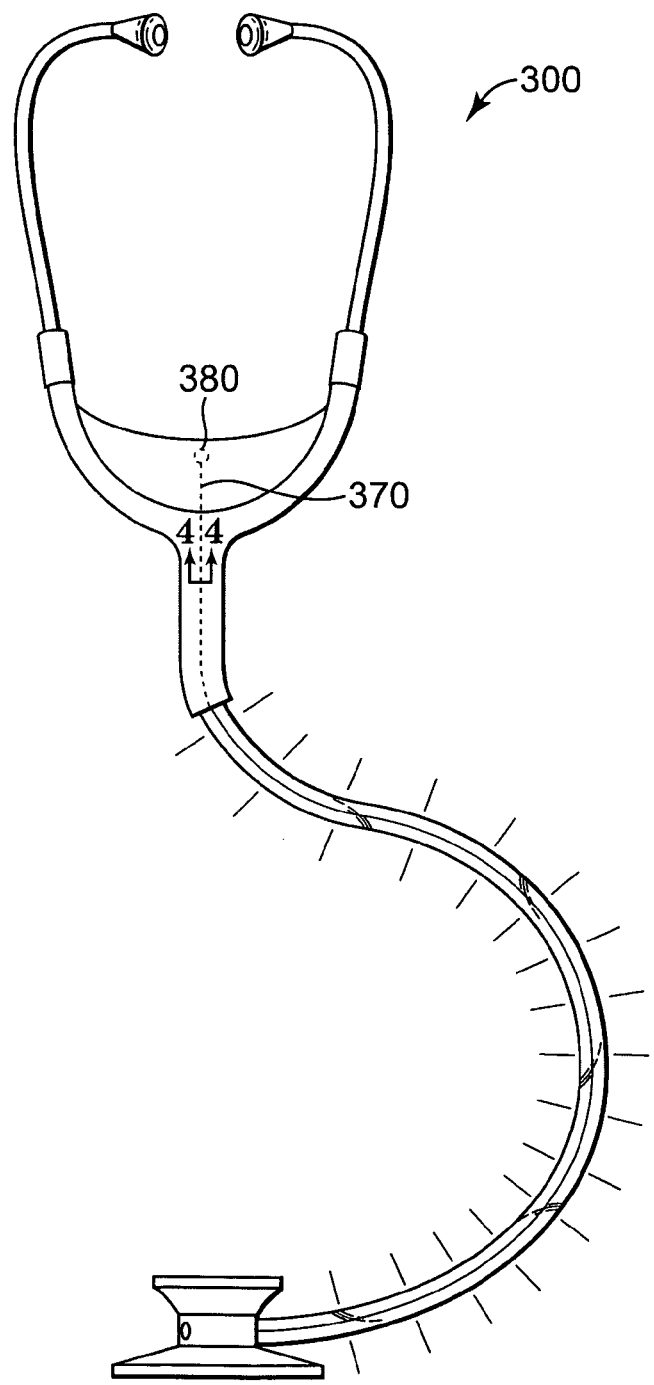
FIG. 3 shows the patient-friendly stethoscope wherein the plastic optical fibers have been impregnated with fluorescent material.

In another embodiment of the present invention depicted in FIG. 3, the patient-friendly stethoscope 300 (and/or chestpiece) may have one or more plastic optical fibers 370 which may have been impregnated with fluorescent materials that radiate colored light specific to the particular fluorescent material used when optically excited. In this configuration a tungsten halogen, or equivalent broadband white light source 380 may be used to optically excite the fluorescent material. The broadband white light source 380 may require a bandpass optical filter to select particular wavelengths which are preferentially absorbed by the fluorescent material. The broadband white light source 380 may be operated continuously or flashed at a low repetition frequency pleasing to the eye.

Figure 4:
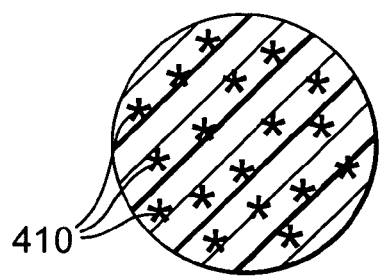
FIG. 4 shows a cross sectional view of an optical fiber shown in FIG. 3 depicting the impregnated fluorescent material distributed within the optical fiber.

In another embodiment of the present invention depicted in FIG. 4, the patient-friendly stethoscope 300 may have one or more plastic optical fibers 370 which may have been impregnated with a phosphor material 410 which may glow in the dark without the need for a broadband white light source 380 as explained above for the fluorescent materials. The phosphor materials 410 typically become energized and emit colored light after being exposed to room light or direct sunlight and continue to emit light for a period of time commonly referred to as the persistence of the phosphor. Two commercially available phosphors which may be useful in impregnating the optical fibers 370 are zinc sulfide and strontium aluminate. In essence, the fibers may be self-illuminating, without the aid of a separate power source to maintain illumination, at least for limited periods of time.

Figures 5, 6:
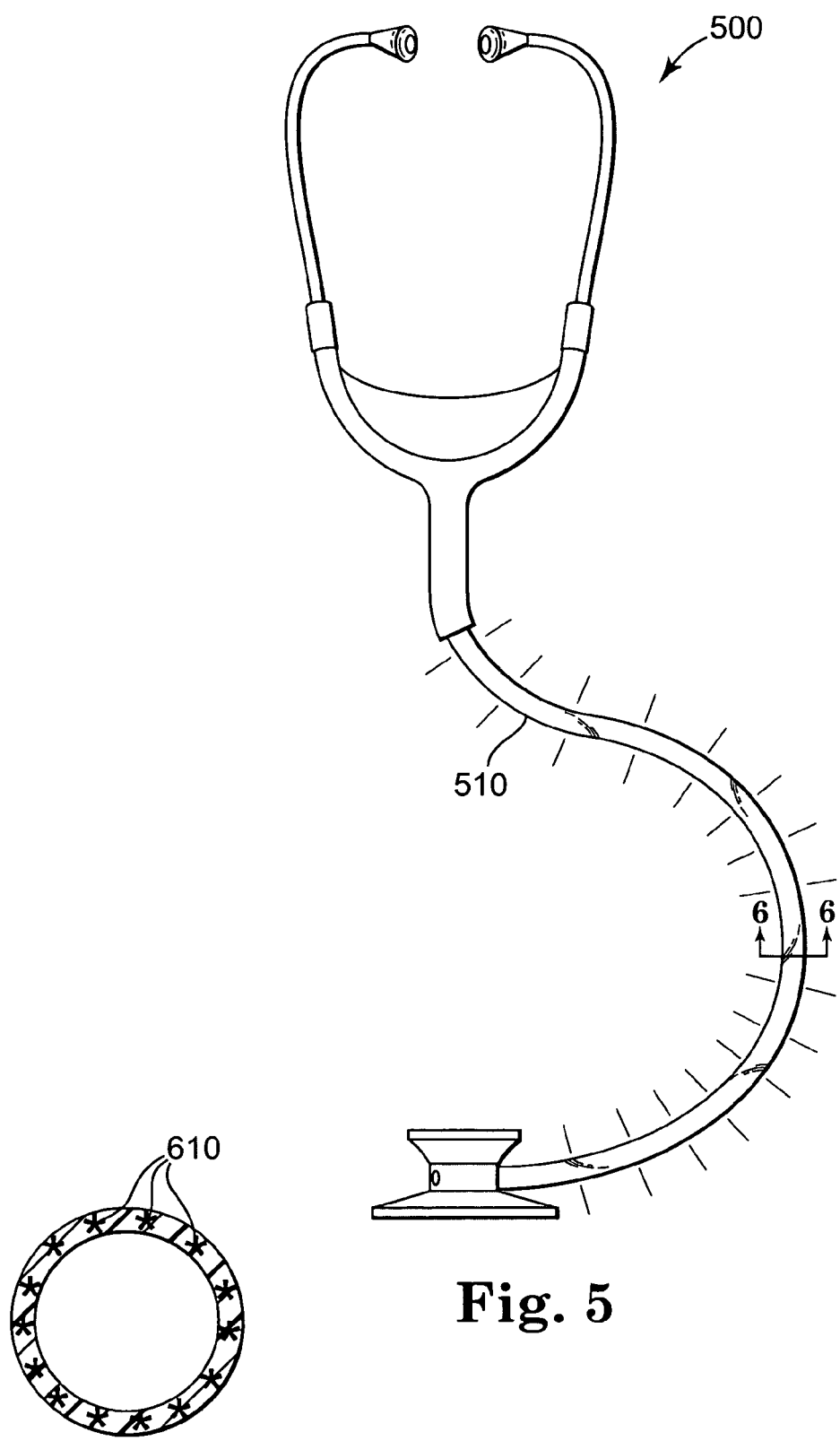
FIG. 5 shows the patient-friendly stethoscope wherein the transparent acoustic tubing has been impregnated with phosphor material.
FIG. 6 shows a cross sectional view of the transparent acoustic tubing depicting the phosphor material distributed within the transparent acoustic tubing.

In another embodiment of the present invention depicted in FIG. 5, the patient-friendly stethoscope 500 may have the transparent acoustic tubing 510 impregnated with a phosphor material (see FIG. 6; item 610) which itself may glow in the dark without the need for either a broadband white light source or for the optical fibers 170 as shown in FIG. 1. As noted above, two commercially available phosphors which may be useful in impregnating the transparent acoustic tubing 510 are zinc sulfide and strontium aluminate.

Figure 7:
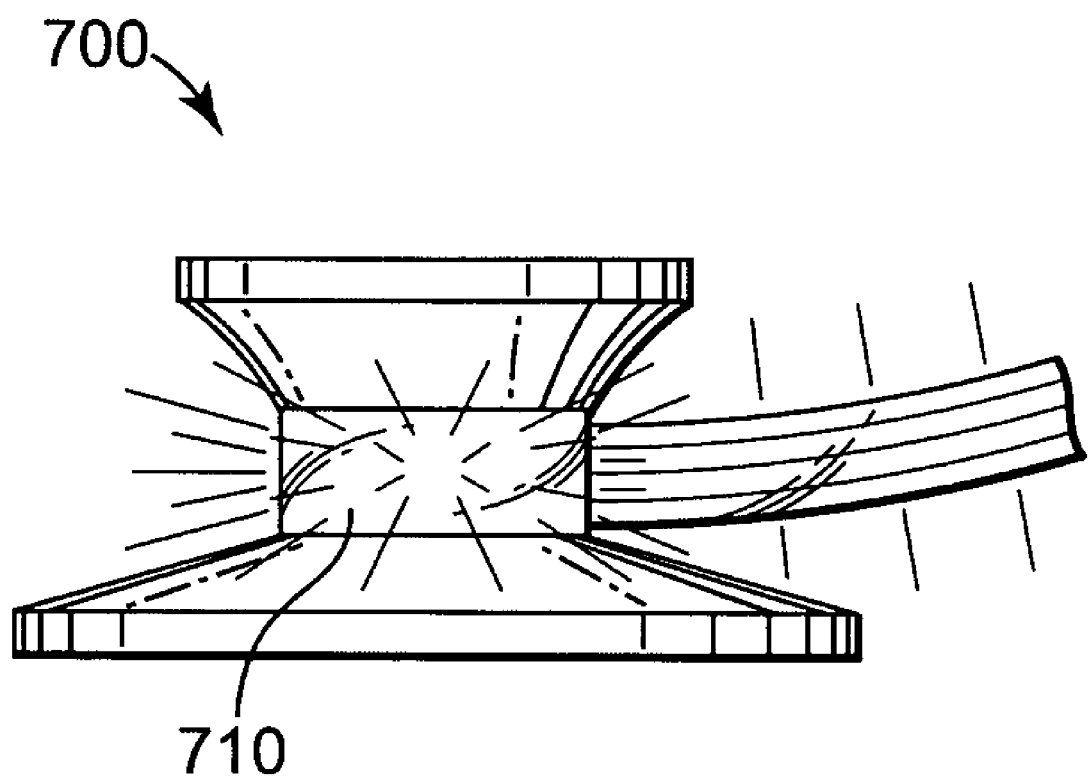
FIG. 7 shows the chestpiece of the patient-friendly stethoscope wherein the annular ring, preferably plastic, of the chestpiece has been impregnated with phosphor material or has a fiber optic illumination source.

In another embodiment of the present invention depicted in FIG. 7, the patient-friendly stethoscope may have a plastic annular ring 710 of the chest piece 700 impregnated with a phosphor material which itself may glow in the dark without the need for either a broadband white light source or for the optical fibers 170 shown in FIG. 1.

Figure 8:
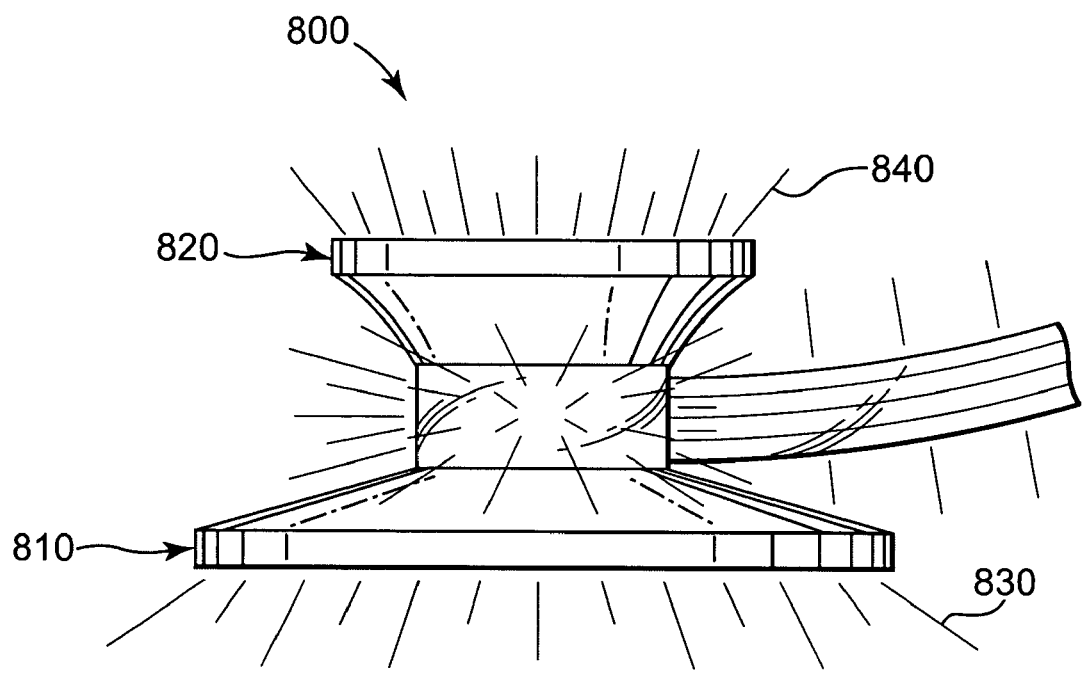

In another embodiment of the present invention depicted in FIG. 8, the patient-friendly stethoscope chestpiece 800 may have the outer rim of the chestpiece diaphragm 810 and the outer rim of the chestpiece bell 820 manufactured with fiber optics as described for the tube or from a plastic material impregnated with a phosphor material which itself may glow in the dark (visible light 830 radiating from diaphragm 810 and visible light 840 radiating from the bell 820) without the need for either a broadband white light source or for the optical fibers 170 shown in FIG. 1. For purposes of this disclosure, "outer peripheral surface" of the chest piece is defined as any peripheral surface, whether it be the outer rim or the annular rim or other areas which may be visible on the chestpiece.

Figure 9:
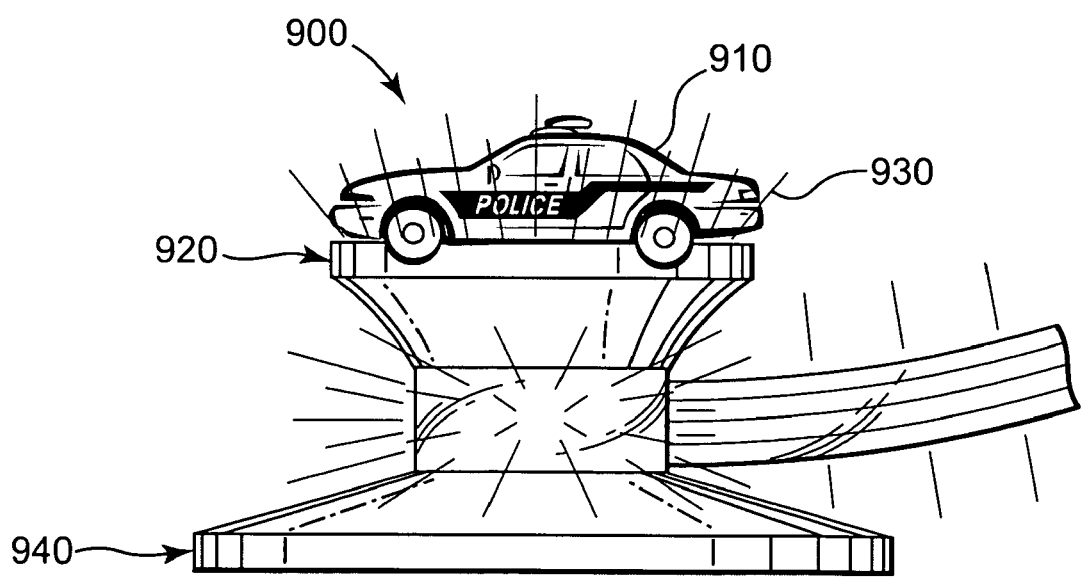
FIG. 9 shows the chestpiece of the patient-friendly stethoscope wherein a child-friendly attachment has been mounted on the bell area of the stethoscope.

In another embodiment of the present invention depicted in FIG. 9, the patient-friendly stethoscope chestpiece 900 may have snap-on attachments such as the police car 910 shown mounted on the stethoscope bell 920. The police car 910 may be manufactured with optical fibers, direct illumination from LEDs or similar or from a material, likely plastic, impregnated with a phosphor material which itself may glow in the dark (visible light 930 radiating from the police car 910) or the police car 910 may be transparent and/or translucent and illuminated by visible light radiating from the stethoscope bell 920 (as shown in FIG. 8; element 820). Additional child-friendly attachments such as fire trucks, airplanes, and the like may be included as well as attaching such devices to both the bell 920 and diaphragm 940 surface.

In another embodiment, the material applied to the tubing 510 can be a heat sensitive temperature responsive material, often made of liquid crystals. These crystals respond to temperature by changing color. Thus a patient or doctor who touches any part of tube will cause it to change color proximate where it is touched, a rainbow effect is generated. With back lighting, by means suggested above, the color combinations of liquid crystals can be made to glow further enhancing its attractiveness.

Using heat sensitive materials, the chestpiece 150 could also vary in color as it is applied to the patient, creating further interest. Indeed, the chestpiece having such a coating and calibrations could also function as a simple skin temp thermometer simultaneously.

It would be possible to insert a sensor into the chest piece (such as a piezo-electric sensor) to sense heart beat or respiration (or other metabolic function) and transmit that data to the circuitry which controls the modulation of the light source (in effect an illumination modulator responsive to stimuli or measurement of metabolic functions, i.e., any measurable parameter on the body). This would permit the patient to see changes in the illumination in response to changes in the measured parameter, for example, pulse or respiration in terms of light amplitude, color shift or other attractive identifiers response to sensed information.

Another embodiment of the invention is all of the above disclosure but directed to an ultrasound device instead of a chest piece 150, such as having an optically illuminated transparent outer tubing. An optical fiber is located within the transparent outer tubing extending from the proximal end of the ultrasound probe to the distal end of the ultrasound probe. The optical fiber has a light source at its proximal end thereby illuminating the transparent outer tubing from within.

Another embodiment of the invention is directed to an ultrasound device having an optically illuminated transparent outer tubing. An optical fiber is located within the transparent outer tubing for internally illuminating the outer transparent tubing from within. The optical fiber is impregnated with a fluorescent dye and a light source is coupled at its proximal end for exciting the fluorescent dye thereby illuminating the transparent outer tubing from within.

Another embodiment of the invention is directed to an ultrasound device having an optically illuminated transparent outer tubing. The transparent outer tubing is impregnated with a phosphor material for internally illuminating the outer transparent tubing from within. The impregnated phosphor material may extend from the proximal end of the ultrasound probe to the distal end of the ultrasonic probe.

Another embodiment of the invention is directed to an endoscope device configured like any of the above embodiments except not being a stethoscope and having an optically illuminated transparent outer tubing or sheath. An optical transmitter or optical fiber is located within the transparent outer tubing extending from the proximal end of the endoscope to the distal end of the endoscope. The optical fiber can have a light source anywhere it can be introduced such as at its proximal end thereby illuminating the transparent outer tubing from within.

Another embodiment of the invention is directed to an endoscope device having an optically illuminated transparent outer tubing. An optical fiber is located within the transparent outer tubing for internally illuminating the outer transparent tubing from within. The optical fiber is impregnated with a fluorescent dye and a light source is coupled at its proximal end for exciting the fluorescent dye thereby illuminating the transparent outer tubing from within.

The endoscope device may also have an optically illuminated transparent outer sheathing/tubing. The transparent outer tubing or the optical transmitter can be impregnated with a phosphor material for internally illuminating the outer transparent tubing from within. The impregnated phosphor material may extend from the proximal end of the endoscope to the distal end of the endoscope.

As noted above, the present invention is directed generally to medical devices and more particularly to a patient-friendly stethoscope with interactive light emissions. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

I claim:

1. A patient-friendly stethoscope comprising;
  a. an earpiece,
  b. a chest piece,
  c. a sound transmitting conduit between said earpiece and chest piece, an optical fiber capable of self-illuminating for externally illuminating the conduit; said optical fiber extending at least partway along said conduit so that a patient will be distracted by the emitted light and away from the medical procedure.

2. The stethoscope of claim 1 wherein said optical fiber is impregnated with a fluorescent dye.

3. The stethoscope of claim 1 wherein said optical fiber is impregnated with a phosphor material.

4. The stethoscope of claim 1 wherein said fiber extends to said chestpiece.

5. The stethoscope of claim 4 wherein said chestpiece includes an outer peripheral edge and wherein said fibers extend to said edge.

6. The stethoscope of claim 5 wherein said fibers are impregnated with fluorescent dye and wherein said fibers include a light source.

7. The stethoscope of claim 5 wherein at least a portion thereof is impregnated with illuminating phosphors.

8. The stethoscope of claim 5 includes an annular ring.

9. The stethoscope of claim 5 wherein said outer peripheral edge is an outer rim.

10. The stethoscope of claim 1 further comprising a snap-on attachment affixable to said chest piece.

11. The stethoscope of claim 1 further comprising a snap-on attachment illuminated by visible light radiating from the stethoscope and affixable to said chest piece.

* * * * *